United States Patent
Moulu et al.

[11] Patent Number: 6,021,662
[45] Date of Patent: Feb. 8, 2000

[54] METHOD FOR MODELING FLUID DISPLACEMENTS IN A POROUS MEDIUM

[75] Inventors: Jean-Claude Moulu, Aubergenville; Olga Vizika, Paris; Francois Kalaydjian, Rueil-Malmaison, all of France

[73] Assignee: Institut Francais Du Petrole, Rueil-Malmaison, France

[21] Appl. No.: 09/166,112

[22] Filed: Oct. 5, 1998

[30] Foreign Application Priority Data

Dec. 15, 1997 [FR] France ................................ 97 15981

[51] Int. Cl.$^7$ ................................................ G01N 15/08
[52] U.S. Cl. ........................................... 73/38; 702/12
[58] Field of Search ............................ 73/37, 38; 702/12

[56] References Cited

U.S. PATENT DOCUMENTS 4,628,468 12/1986 Thompson et al. ................. 702/12

*Primary Examiner*—Hezron Williams
*Assistant Examiner*—Jay Politzer

*Attorney, Agent, or Firm*—Antonelli, Terry, Stout & Kraus, LLP

[57] ABSTRACT

Modelling method for optimizing faster and more realistically the displacement conditions, in a porous medium wettable by a first fluid (water for example), of a mixture of fluids including this wetting fluid and at least another fluid (oil and possibly gas). The method comprises experimental determination of the variation curve of the capillary pressure in the pores as a function of the saturation in the liquid phases, modelling the pores of the porous medium by means of a distribution of capillaries with a fractal section while considering, in the case of a three-phase water (wetting fluid)-oil-gas mixture for example, a stratification of the constituents in the pores, with the water in contact with the walls, the gas in the center and the oil forming an intercalary layer, determination, from this capillary pressure curve, of the fractal dimension values corresponding to a series of given values of the saturation in the liquid phase, modelling the relative permeabilities directly in the form of analytic expressions depending on the various fractal dimension values obtained and in accordance with the stratified distribution of the various fluids in the pores, and using a porous medium simulator in order to determine, from the relative permeabilities, the optimum displacement conditions of the fluids in the porous medium. The method can be applied for petroleum production, soil depollution, etc.

4 Claims, 2 Drawing Sheets

| Sg=0 | 0.01 | 0.05 | 0.10 | 0.15 | 0.20 | 0.25 | 0.30 | 0.35 | 0.40 | 0.45 | 0.50 | 0.55 | Sw |
|---|---|---|---|---|---|---|---|---|---|---|---|---|---|
|  |  |  |  |  |  |  |  |  | .30 |  |  |  | 0.40 |
| 0 Displ.1 | .002 | .014 | .04 | .08 | .13 | .20 | .27 | .34 .20 | .46 | .57 | .68 | .83 | 0.44 |
|  |  | 0.007 | 0.02 | 0.046 | 0.081 | .117 | .205 | 0.28 | 0.39 | 0.48 | 0.57 |  | 0.50 |
|  |  | 0.004 | 0.011 | 0.025 | .042 | 0.067 | 0.14 | 0.22 | 0.30 | 0.40 |  |  | 0.55 |
| 0 Displ.3 | .0002 | .0017 | .006 | .0145 | 0.032 | 0.06 | .106 | .175 | 0.25 |  |  |  | 0.60 |
|  |  | 0.0007 | 0.0025 | 0.006 | 0.019 | .037 | 0.070 | 0.11 |  |  |  |  | 0.65 |
|  |  | 0.0003 | 0.0012 | .004 | .01 | 0.023 | 0.045 |  |  |  |  |  | 0.70 |
|  |  | .0001 | .0005 |  |  | 0.015 |  |  |  |  |  |  | 0.75 |
| 0 Displ.2 | 0 |  |  |  |  |  |  |  |  |  |  |  | 0.80 |

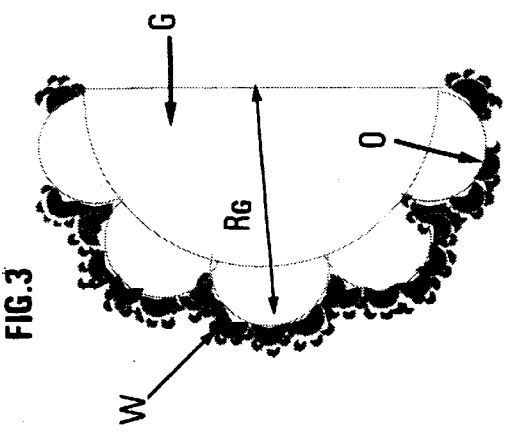
FIG.1
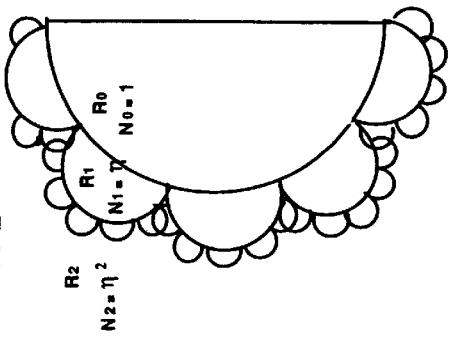
FIG.3
FIG.2

METHOD FOR MODELING FLUID DISPLACEMENTS IN A POROUS MEDIUM

FIELD OF THE INVENTION

The present invention relates to a method for modelling two-phase or three-phase flows in a porous medium, based on a fractal representation thereof.

The method according to the invention is applicable in many fields where fluid flows in porous media are to be modelled in order to optimize the conditions of the displacement thereof. Examples of fields of application are:

a) development of an oil reservoir and notably enhanced oil production by injection of fluids, using for example alternating injections of liquid and gas slugs (a method referred to as WAG);

b) soil depollution and notably depollution of industrial sites by injection of substances such as surfactants in polluted layers;

c) cleaning of filter cakes by displacement of the substances retained therein;

d) wood drying;

e) optimization of chemical reactions for example by displacement of reaction products in a catalyst mass in order to increase the surfaces of contact, etc.

The method according to the invention is directly applicable by reservoir engineers in order to determine, for example, the most suitable enhanced recovery method to be applied to an underground hydrocarbon reservoir. The method can also serve within the scope of industrial site depollution operations for example.

BACKGROUND OF THE INVENTION

1) Experimental studies

Experimental determination of the relative permeabilities of a porous medium wherein a multiphase fluid flows is not easy. Measuring operations are usually simplified by considering that one of the phases is immobile in a state of irreducible saturation.

The values are for example acquired by means of a well-known experimental method referred to as "steady state" for determining relative permeabilities, which consists in allowing a three-phase fluid to flow with imposed flow rates between the phases. The relative permeabilities expressed as a function of the two saturations are calculated by applying Darcy's law to each phase. It is not an established fact that the relative permeability measurements obtained by means of this method are really representative of the fluid displacements and in any case they take a long time because, at each regime change, one has to wait for a state of equilibrium.

Another known method consists in carrying out laboratory tests in order to determine measurement tables (as shown in FIG. 1) relating the relative permeabilities and the saturations for each pair of fluids of the three-phase mixture. By adjusting experimental production curves, one tries to progressively adjust the three-phase relative permeabilities. These data tables are then fed into a Score® or Athos® type numerical simulator which computes the fluid productions. This method being based on the prior acquisition of many experimental measurements progressively adjusted by calibration, it takes a long time.

Another known experimental measuring method is described for example in patents FR-A-2,708,742 or 2,724,460 filed by the applicant. It is implemented by placing in a measuring cell a bar cut in the porous medium to be studied and containing, at variable saturations for each experiment, two phases of a three-phase fluid. A third phase of this fluid is injected at one end of the bar and the production of the three phases as a function of time is recorded at the opposite end.

2) Models

The known empirical model referred to as Stone's model allows, by empirical correlations, to predict data relative to a three-phase flow from data corresponding to a two-phase flow. It is valid only in case of a high water wettability and it is generally considered to be poorly predictive.

There are two known types of physical models for modelling three-phase flows, based on capillary pressure curves. The latter generally include a pseudo-plateau with a gentle slope corresponding to the largest pores, therefore to the lowest mercury pressures, and one or more more or less linear parts with a steep slope. The capillary pressure curves are connected with a saturation (for example that of the mercury injected) and a pore radius from which the mercury stops for a given injection pressure determined by Laplace's law, $P_{inj} = 2 \, s.r$.

A first porous media representation model is described by:

Burdine, N. T. : "Relative permeability calculations from pore size distribution data", *Trans AIME* (1953), Vol.198, or by Corey, A. T.: "The interrelation between oil and gas relative permeabilities", *Prod. Monthly* (1954), Vol.19, 38.

According to this model, the porous model is represented by a bundle of cylindrical capillaries with a radius distribution given by the capillary pressure curve obtained by mercury injection. The permeabilities are obtained by applying Poiseuille's law to the flow of fluids in these capillaries.

This model is based on the representation of the porous medium as an assembly of capillaries with different radii. The relation between the volume and the radius of the pores is given by the value of the slope of the pseudo-plateau. The three fluids are supposed to share the capillaries between them, the wetting fluid (water) occupying the smallest pores, the least wetting fluid (gas) the largest pores and the third fluid (oil) a zone with intermediate-size pores. It is not possible to describe the interactions between the fluids because, in such a model, they flow through separate channels. Finally, this model can be useful only if the pseudo-plateau covers a wide range of saturations. According to this model, the three phases of a three-phase flow move in different capillaries and there is no interaction between them.

Another known physical porous medium representation model is described by:

de Gennes, P. G. : "Partial Filling of a Fractal Structure by a Wetting Fluid". Physics of Disordered Materials 227–241, New York Plenum Pub. Corp. (1985), or by Lenormand, R.: "Gravity Assisted Inert Gas Injection: Micromodel Experiments and Model based on Fractal Roughness", The European Oil and Gas Conference Altavilla Milica, Palermo, Sicily (1990).

According to this model, one considers that the inner surface of the pores is isotropic and has a fractal character, and it can be modelled as a "bunch" of parallel capillary grooves so that the pores exhibit a fractal cross section. The cross section of each pore is constructed according to an iterative process (FIG. 1). The half-perimeter of a circle of radius $R_0$ is divided into η parts and each of these η parts is replaced by a semi-circle or groove. At each stage k of the process, $N_k$ new semi-circular grooves of radius $R_k$ and of total section $A_k$ are created.

The fractal dimension DL of the cross section at the end of stage k is related to the number of objects Nk generated with the given scale $I_k$ by the relation:

$$N_k \infty I_k^{-D_L}$$

The fractal dimension can be deduced from a mercury capillary pressure curve according to the following procedure. Mercury is injected into a porous medium with an injection pressure that increases in stages. Laplace's law allows to deduce the pore volume, knowing the volume of mercury injected for a given capillary pressure and one can construct the drainage capillary pressure curve relating the injection pressure to the amount of mercury injected and the curve relating the proportion of the total volume occupied by the pores to the size of the pores. In cases where a wetting liquid is drained from the porous medium such as water by injecting gas, the correlation between the gas-water capillary pressure and the saturation of the wetting phase is given by:

$$P_c = S_W^{\frac{1}{D_L-2}}$$

In this log-log representation, the slope $1/(D_L-2)$ of each line (from −1.5 to −3.3) gives the value of the linear fractal dimension $D_L$ between 1.3 and 1.7.

The experimental results readily show that the values of the gas-water relative permeabilities expressed as a function of the three saturations, obtained from the expressions given by the known models and the phase distribution modes in the structure of the pores, are far from the measured values and therefore that the models concerned prove to be too simplistic to represent the complex interactions that take place between the fluid phases.

SUMMARY OF THE INVENTION

The modelling method according to the invention allows to optimize faster and more realistically the displacement conditions, in a porous medium wettable by a first fluid, of two-phase or three-phase mixtures including this first wetting fluid and at least a second fluid. It therefore provides operators with a more reliable tool for evaluating notably the best displacement modes of the fluids in the porous medium.

It is characterized in that it comprises in combination:

experimental determination of the variation curve of the capillary pressure (Pc) in the pores of a sample of this porous medium in the presence of a wetting fluid and of a non-wetting fluid (by injection of mercury in a sample placed under vacuum for example);

modelling of the pores of the porous medium by means of a distribution of capillaries with a fractal section while considering a stratified distribution of the fluids in the pores, the wetting fluid spreading out in contact with the walls and around the second fluid (or the two others in case of a three-phase mixture);

determination, from this capillary pressure curve, of the fractal dimension values corresponding to a series of given values of the saturation in liquids;

modelling of the relative permeabilities directly in the form of analytic expressions depending on the various fractal dimension values obtained, and entry of the relative permeabilities in a porous medium simulator and determination, by means of this simulator, of the optimum displacement conditions of the fluids of the mixture in the porous medium.

The method is applied for example for determining displacements of fluid mixtures comprising a first wetting fluid, a second non-wetting fluid and a gas, considering a stratified distribution of the fluids in the pores, the wetting fluid spreading out in contact with the walls, the gas occupying the centre of the pores and the second fluid being distributed in the form of an annular layer in contact with both the gas and the first fluid.

The method can notably be applied for determining, by means of a reservoir simulator, the optimum characteristics of substances added to wetting fluid slugs injected in a formation alternately with gas slugs, in order to displace hydrocarbons in place, or those of a fluid injected into the soil in order to displace polluting substances.

The phenomena modelling obtained by means of the method has many advantages. It allows a better correspondence with the results obtained in the laboratory because the physical phenomena are better taken into account. The results of the model are therefore better in case of a scale change for example, for modelling an application in an operation field.

The calculating time is reduced by comparison with the time required when tables are used as in the prior methods. Fractal type modelling can better deal with the hysteresis effects encountered when using WAG type injection processes.

The results of the method can furthermore be perfectly integrated into many reservoir simulators: 3D, heterogeneous, composition simulators, etc.

Exploitation of the results by application softwares is facilitated. It is no longer necessary to perform risky interpolations as it is the rule when working from discrete values of the result tables in order to draw isoperms for example.

BRIEF DESCRIPTION OF THE DRAWINGS

Other features and advantages of the method according to the invention will be clear from reading the description hereafter of a non limitative example, with reference to the accompanying drawings wherein:

FIG. 1 illustrates, in the form of a table, the connections existing for a three-phase mixture between the experimentally obtained relative permeability values of a fluid and the saturations for two of the three fluids, FIG. 2 is a fractal representation of a pore, FIG. 3 diagrammatically shows the distribution of the phases of a three-phase fluid in a fractal pore with the wetting fluid W in contact with the wall, the gas phase G spread over the greatest part of the volume of the pore (radius $R_G$), the non-wetting fluid O being a layer between the wetting fluid and the gas.

DETAILED DESCRIPTION OF THE METHOD

The method according to the invention allows to determine the three-phase relative permeabilities of porous media by using a fractal type model of the porous medium, on the basis of an approach described by:

Kalaydjian, F. J-M et al.: "Three Phase Flow in Water-wet Porous Media: Determination of Gas-oil Relative Permeabilities under Various Spreading conditions", 68th Ann. Tech. Conf. and Exh. of the SPE, Houston, Tex., 1993.

Description of the Invention

The method according to the invention comprises, as stated above, modelling of the flow of the phases with distribution of the phases in the fractal structure of each pore. In case of water and oil flowing in a water wet porous structure, the oil flows into the volume of the pore. In case of a three-phase flow, there is a stratified distribution, the water, which is the wetting fluid, flows along the walls of the pores, the gas circulates in the volume of the pore and the oil flows between the gas and the water. The saturations are calculated as the relative surface area in a cross section occupied by each of the fluids. At equilibrium, all the grooves having a radius less than or equal to Rk, which is given by Laplace's law $Pc=2\gamma/R_k$, are occupied by the wetting fluid, and the largest tubes by the non-wetting fluid. The wetting fluid saturation is thus expressed as the fraction of the occupied area of the tubes.

Calculation of the fraction of the area of the capillaries occupied by the water for all the radii between $R_k$ and $R_\infty$ leads to the following expression:

$$S_w = \left[\frac{R_k}{R_0}\right]^{2-D_L}$$

and as $Pc=2\gamma/R_k$, the correlation between the capillary pressure and the saturation of the wetting phase is given by:

$$Pc = Sw^{\frac{1}{D_L-2}}$$

where Sw is the saturation of the wetting phase.

Figure 4:
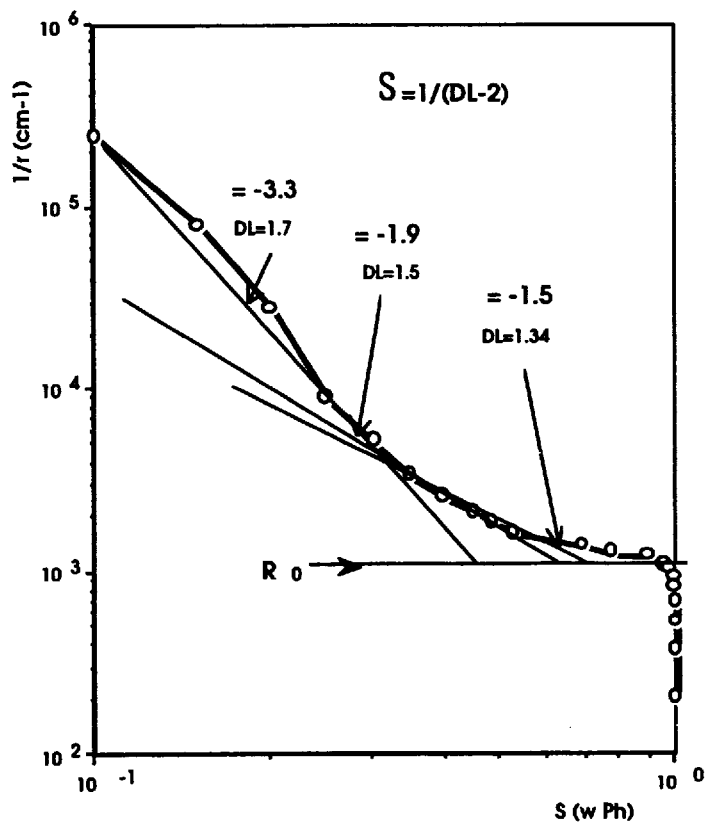
FIG. 4 shows, as a function of the water saturation, the capillary pressure curve of a sample of Vosges sandstone for example, whose local slope S is used to determine the fractal dimension of the pores.

The graphical representation of this correlation in a log-log diagram is a straight line starting from the point (Sw, Pc) corresponding to the largest capillary of the fractal structure with a radius $R_0$. One may suppose that (FIG. 4):

radius $R_0$, which is first invaded when mercury is injected, corresponds to a saturation value of the order of $1/r = 10^3$. Each segment of the capillary pressure curve is a part of a line starting from $R_0$ (assumed to be the same for all the different segments), corresponding to the aforementioned correlation Pc, Sw. Each line has a given slope, a fractal linear dimension can be associated therewith. The values of the slope range from −1.5 to −3.3 as shown in FIG. 4, which leads to values of the fractal linear dimension $D_L$ between 1.3 and 1.7;

each domain is reached by the mercury for saturations corresponding to the place where $R_0$ is found on each line.

The saturation of the two liquids when the gas is present in the pore is calculated as explained above for a phase:

$$S_{Liq.} = \left[\frac{R_k}{R_0}\right]^{2-D_L}$$

assuming that the two liquids occupy tubes whose radii are less than or equal to $R_k$ and the gas, the centre of each pore. The oil saturation is the relative area of the cross section of the grooves occupied by oil, whose radius is less than or equal to $R_k$.

Calculation of the relative permeabilities requires determination, for each phase, of the fraction circulating therein and consequently systematic estimation of the saturations corresponding to the stagnant fractions. This must be done for the two cases studied, for example drainage of water and oil by gas, and water imbibition.

Calculation of the Relative Permeabilities

Relative permeabilities of liquids

Figure 5:
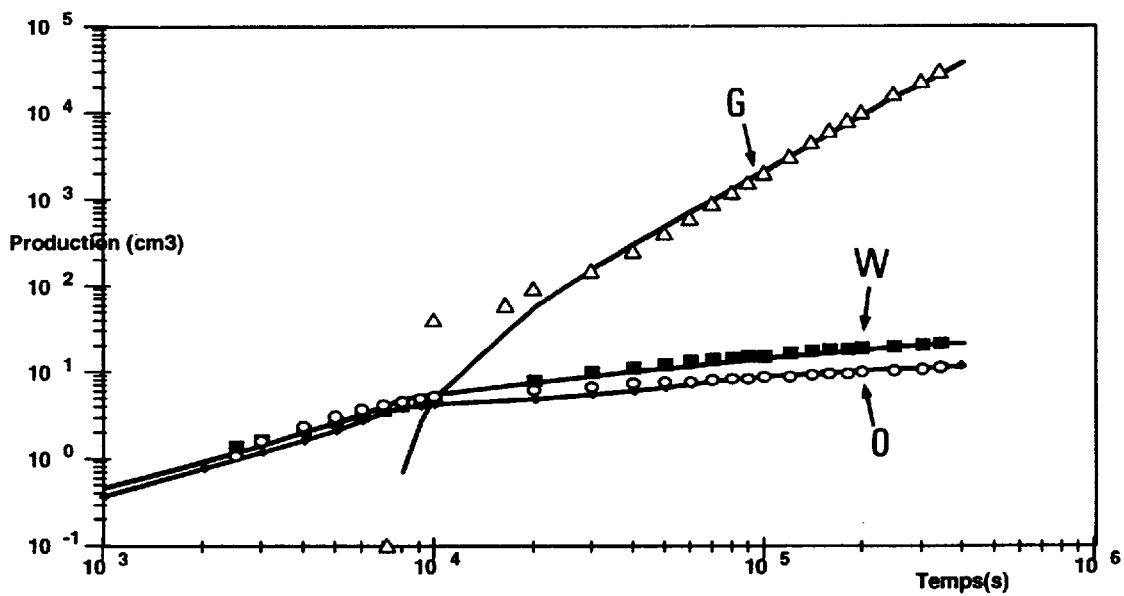
FIG. 5 shows, as a function of time, the production curves obtained experimentally for gas (G), for water (W) and for oil (O), compared with the equivalent curves obtained by simulation by means of the method according to the invention.

Application of Poiseuille's law to each capillary of the bundle occupied by the phase which occupies it allows to calculate the water and oil relative permeabilities (FIG. 5).

If we consider only the circulating fraction which contributes to the hydraulic conductivity, the relative permeabilities for water and oil are expressed as follows:

$$k_{rw} = S_w^{\frac{4-D_L}{2-D_L}} - S_{wi}^{\frac{4-D_L}{2-D_L}} \tag{1}$$

$$k_{ro} = k_{ro}(2\ Ph.)\left[S_L^{\frac{4-D_L}{2-D_L}} - (S_W + S_{or})^{\frac{4-D_L}{2-D_L}}\right] \tag{2}$$

In these expressions, it is useful to mention that:

the irreducible water saturation Swi is assumed to be stable,

Sorw is the saturation in residual oil left in place after sweeping the medium with water and Sor is a part of this residual saturation which corresponds to a determined water saturation, the size range of capillaries occupied by the moving oil is calculated as the difference between the sizes of the capillaries occupied by the two liquids with the total liquid saturation $S_L = S_o + S_w$ and those of the capillaries saturated in water and stagnant oil, $k_{ro}$(2 ph.) is the value of the oil relative permeability determined by an imbibition test with water and oil. When only the water and the oil are present and since the sample tested is water wet, the oil will flow through the section of the pore exactly as the gas in a three-phase flow.

Gas relative permeability

Since gas is a non-wetting phase, it occupies the central space of the pore and it spreads towards the periphery thereof as the gas saturation increases, however without coming into contact with the solid wall (FIG. 6). One considers that the gas circulates in a single pore whose radius $R_g$ is given by the relation as follows:

$$R_g = R_0 + R_1 + R_2 + \ldots + R_k,$$

the gas permeability being then given by:

$$k_{rg} = k_{rgmax.}(1 - S_L^\alpha)^4 \tag{4}$$

with $$\alpha = \frac{1}{2 - D_L}, D_L$$

being the linear fractal dimension of the porous medium and $S_L$ the total liquid saturation equal to $1-S_g$.

After determining the water, oil and gas relative permeabilities, $k_{rw}$, $k_{ro}$ and $k_{rg}$ respectively, a reservoir simulator suited to laboratory conditions, such as the ΣCORE® simulator for example, is used according to a known procedure described for example by:

Moulu J. C. et al: "Performance and Numerical Interpretation of Gas Drainage Core Tests under Secondary and Tertiary Conditions", Paper SCA 9508, SCA Symposium, San Francisco, September 1995.

The conditions to be satisfied in order to displace petroleum fluids in place in a reservoir, either by gas injection or by alternate injection of water and gas slugs (a method referred to as WAG), can thus be readily optimized by taking account of the pressure and temperature conditions prevailing at the production depth.

Validation

The method according to the invention has been validated by performing gas injections in porous media containing water and oil, under various conditions. It can be seen in FIG. 5 for example that a very good accordance is obtained between the production curves of the three phases (water, oil, gas) obtained experimentally and those predicted by the reservoir simulator fed with the data obtained in accordance with the method.

We claim:

1. A modelling method for optimizing displacement conditions, in a porous medium wettable by a first liquid, of a mixture of two-phase or three-phase fluids including the first wetting liquid and a second non-wetting liquid, comprising:

experimentally determining a variation curve of the capillary pressure ($P_C$) in pores of a sample of said porous medium in presence of the wetting liquid and the non-wetting liquid;

modelling pores of the porous medium by a distribution of capillaries with a fractal section while considering a stratified distribution of the fluids in the mixture in the pores, the wetting spreading out in contact with walls of the pores and around said another fluid;

determining, from said capillary pressure curve, fractal dimension values corresponding to a series of given values of saturation of the sample in the liquids;

modelling relative permeabilities directly in the form of analytic expressions depending on the different fractal dimension values obtained, and feeding the relative permeabilities into a porous medium simulator and determining, by means of said simulator, optimum displacement conditions for the mixture of fluids in the porous medium.

2. A method as claimed in claim 1, applied to mixtures of fluids comprising a first wetting liquid, a second non-wetting, liquid and a gas, wherein the pores of the porous medium are modelled by a distribution of capillaries with a fractal section while considering a stratified distribution of the fluids in the pores, the wetting liquid spreading out in contact with the walls, the gas occupying the centre of the pores and the second liquid being distributed in the form of an annular film in contact with both the gas and the first liquid.

3. A method as claimed in claim 1, wherein the reservoir simulator is used to determine optimum characteristics of substances added to wetting liquid slugs injected in a formation alternately with gas slugs in order to displace hydrocarbons in place.

4. A method as claimed in claim 1, comprising using a reservoir simulator in order to determine the optimum characteristics of a fluid mixture injected in the soil in order to drain polluting substances.

* * * * *